United States Patent
Bowsher (10) Patent No.: US 8,820,181 B2
(45) Date of Patent: Sep. 2, 2014

(54) GRAIN SAMPLER AND METHOD OF SAMPLING GRAIN FLOW

(75) Inventor: Neil Bowsher, Sullivan, IL (US)

(73) Assignee: The GSI Group, LLC, Assumption, IL (US)

(*) Notice: Subject to any disclaimer, the term of this patent is extended or adjusted under 35 U.S.C. 154(b) by 529 days.

(21) Appl. No.: 13/180,192

(22) Filed: Jul. 11, 2011

(65) Prior Publication Data

US 2012/0011922 A1  Jan. 19, 2012

Related U.S. Application Data

(60) Provisional application No. 61/364,199, filed on Jul. 14, 2010.

(51) Int. Cl.
| | |
|---|---|
| *G01N 1/00* | (2006.01) |
| *G01N 35/04* | (2006.01) |
| *G01N 25/56* | (2006.01) |
| *G01N 1/20* | (2006.01) |
| *G01N 33/00* | (2006.01) |

(52) U.S. Cl.
CPC .. *G01N 1/20* (2013.01); *G01N 1/00* (2013.01); *G01N 25/56* (2013.01); *G01N 35/04* (2013.01); *G01N 2001/2007* (2013.01); *G01N 2033/0091* (2013.01)
USPC .......................................................... 73/863

(58) Field of Classification Search
CPC ........... G01N 1/286; G01N 1/00; G01N 1/38; G01N 1/20; G01N 35/04
USPC ........................................................... 73/863
See application file for complete search history.

(56) References Cited

U.S. PATENT DOCUMENTS

| | | |
|---|---|---|
| 5,604,996 A | 2/1997 | Bestwick et al. |
| 5,651,193 A | 7/1997 | Rhodes et al. |
| 5,724,912 A | 3/1998 | Cull |

*Primary Examiner* — Hezron E Williams
*Assistant Examiner* — Rodney T Frank
(74) *Attorney, Agent, or Firm* — Polster, Lieder, Woodruff & Lucchesi, L.C.

(57) ABSTRACT

A sampler improves sampling and moisture measurements by reducing the introduction of fines, providing a more representative grain sample, and improving the ability to make consistent moisture measurements. The sampler has a body positioned to receive grain from a grain flow path. A primary auger positioned within the body has a shaft and a fin configured to lift and propel a portion of the grain up to and through a sampling opening. A sensor assembly operatively connected to the body and in communication with the sampling opening is configured to receive the portion of grain indicate the moisture content of the portion of grain.

24 Claims, 14 Drawing Sheets

GRAIN SAMPLER AND METHOD OF SAMPLING GRAIN FLOW

CROSS-REFERENCE TO RELATED APPLICATIONS

This Non-Provisional application claims priority to U.S. Provisional Application Ser. No. 61/364,199 filed Jul. 14, 2010, and which is incorporated herein by reference.

STATEMENT REGARDING FEDERALLY SPONSORED RESEARCH

Not applicable.

BACKGROUND OF THE INVENTION

This invention relates to a sampler for measuring a characteristic of a material or product flowing in a path; and, in particular, a sampler for measuring the moisture content of a sampling of grain flowing within a grain dryer.

Grain moisture samplers are typically mounted adjacent to an output path of a grain dryer. The sampler receives a portion of the grain moving toward the outlet discharge of the dryer and presents the grain for moisture measurement. A moisture sensor of the sampler measures and provides an indication of grain moisture. In typical configurations, grain falls into the sampler by gravity and flows out of the sampler by gravity or some mechanical means (i.e., small auger, etc.) The moisture sensor is positioned at some point in the sampler to measure the moisture of the entrapped grain. After being measured for moisture, the grain is returned to the outlet path of the dryer. It will be understood that the moisture sensor indicates the moisture of the dried grain as it is conveyed from the grain dryer. The output of the moisture sensor is sensed by the control system and is used to control the rate (speed) of the metering rolls so as to dry the grain a desired amount.

Due to the position of the sampling opening and the use of gravity infeed to the sampling opening, moisture samplers often are not located in an ideal position and collect foreign material or fines. These foreign material or fines negatively impact the accuracy of moisture measurements. Furthermore, due to spatial constraints and the typical use of inclined augers to move material through the sampler to the outlet, the sampler may not be emptying of sampled grain or foreign material at an appropriate speed. If the auger moves too fast, the moisture sensor may not be fully immersed in a consistent grain mass. Conversely, if the auger moves too slowly, the sensor may not be measuring grain representative of the current flow of grain. Accurate moisture measurement is further complicated by the variation in drying rates during dryer operation.

There is a need for farmers or other grain operators to have grain samplers that accommodate low and high material flow rates without compromising the accuracy of the measurements. Additionally, there is a need for samplers which must be able to reduce the introduction of fines or other debris toward the sensor so that a more representative grain sample to be measured.

BRIEF DESCRIPTION OF THE SEVERAL VIEWS OF THE DRAWINGS

In the accompanying drawings which form part of the specification.

Corresponding reference characters represent corresponding parts throughout the various views of the drawings.

DETAILED DESCRIPTION OF A PREFERRED EMBODIMENT

The following detailed description illustrates the disclosed invention by way of example and not by way of limitation.

The description clearly enables one skilled in the art to make and use the disclosed invention, describes several embodiments, adaptations, variations, alternatives, and uses of the disclosed invention, including what is presently believed to be the best mode of carrying out the disclosed invention.

The disclosure relates to a sampler for sensing moisture characteristics of a product. The sampler is configured to reduce the introduction of foreign material and/or fines toward the sensor; to provide an enhanced representative sample and to improve the consistency of moisture measurements. The sampler can be used for any material flow path as desired. However, for purposes of illustration only, the sampler will be described for use with a grain dryer.

Components of the sampler can have a variety of cross sectional shapes such as, but not limited to, elliptical, oval, circular, triangular, square, rectangular, tubular or other appropriate geometric configuration. Components of the sampler can be made of a variety of materials, such as, but not limited to, steel, cast iron, aluminum or plastic. The sampler can be of any size to accommodate characterizations of users of any size and to accommodate characterizations of product materials and of output paths of dryers of varying cross-sectional shapes and sizes.

The illustrative sampler shown in the drawings may be used with a variety of grain dryers, but the sampler will herein be described in conjunction with a portable or modular grain dryer that may be operated in continuous batch, staged automatic, or continuous flow drying modes. The operation of such portable grain dryers is well known to those skilled in the art and for the sake of brevity, the construction and operation of such dryers is not fully herein described. The construction and operation of such portable dryers are more fully described in U.S. Pat. No. 5,651,193 which is herein incorporated by reference.

Figure 1:
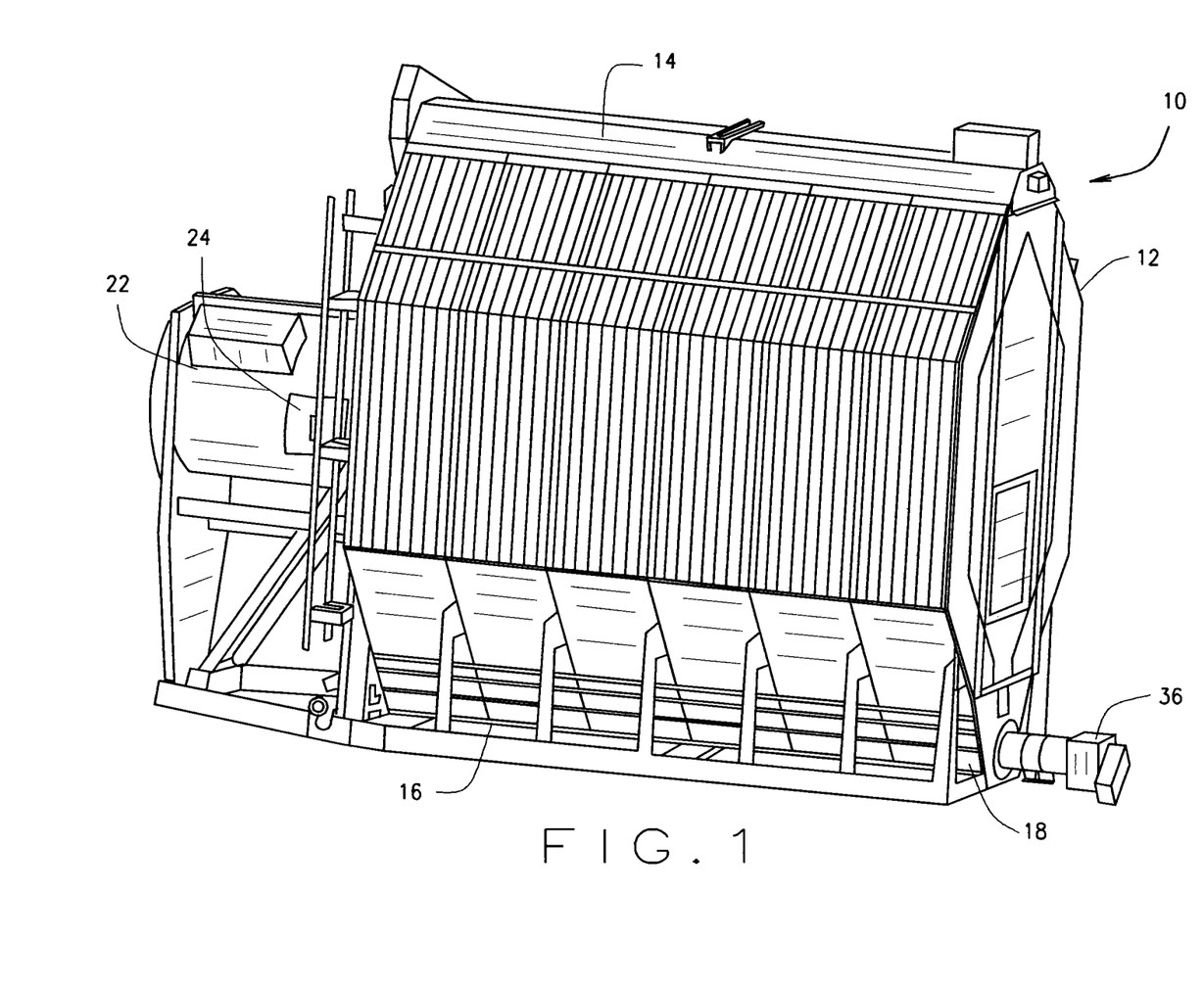
FIG. 1 is a front perspective view of a portable or modular grain dryer having a grain sampler, the sampler being shown operatively connected with a discharge opening of the portable grain dryer.
Figure 1A:
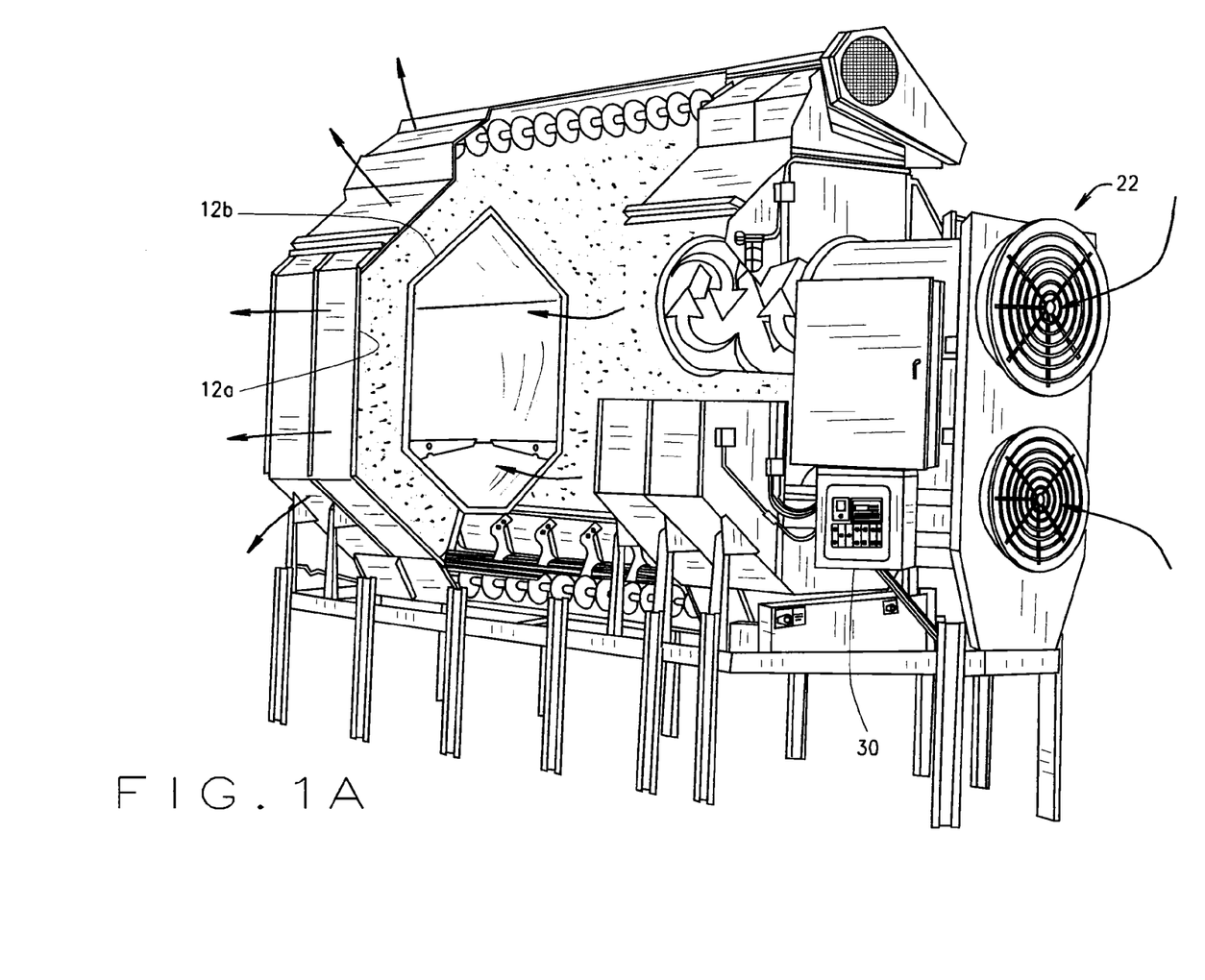
FIG. 1*a* is a cut-away perspective view of a typical portable grain dryer.
Figure 1B:
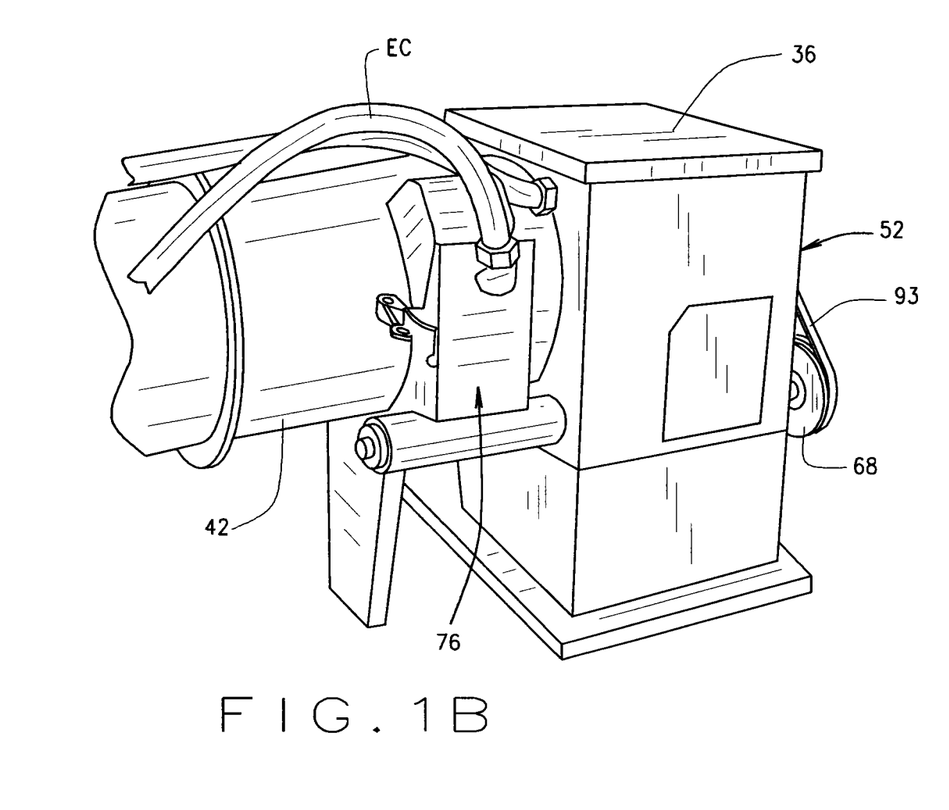
FIG. 1*b* is an exterior view of an embodiment of the sampler.

Turning to FIGS. 1-1b, briefly, a typical, portable grain dryer 10 comprises a housing 12 having an outer basket or wall 12a of perforate construction and an inner basket or wall also of perforate construction with the inner basket or wall 12b spaced from the outer basket or wall a desired distance so as to form a column of grain to be dried. The wet grain to be dried is delivered to a horizontal garner bin 14 at the top of the dryer 10 and is distributed lengthwise of the dryer. Both the inner and outer baskets or walls are usually concentric relative to one another and are in the form of a vertically disposed diamond shaped (when viewed in cross section) grain column such that wet grain from the garner bin 14 is split into two columns, one on each side of the inner basket/wall, by the upper pointed end of the inner basket such that substantially equal quantities of grain flow down the path defined by the grain columns on each side of the inner basket. One or more fans/heater units at one end of the dryer forces heated air into the interior of the inner basket such that the inner basket constitutes a drying or plenum chamber. The heated air is generally uniformly distributed in the plenum chamber and is forced through the perforate inner basket/wall into the grain column to dry the grain in the grain column. The air with the moisture from the grain is discharged to the atmosphere as it passes through the perforate outer basket/wall.

Figure 1C:
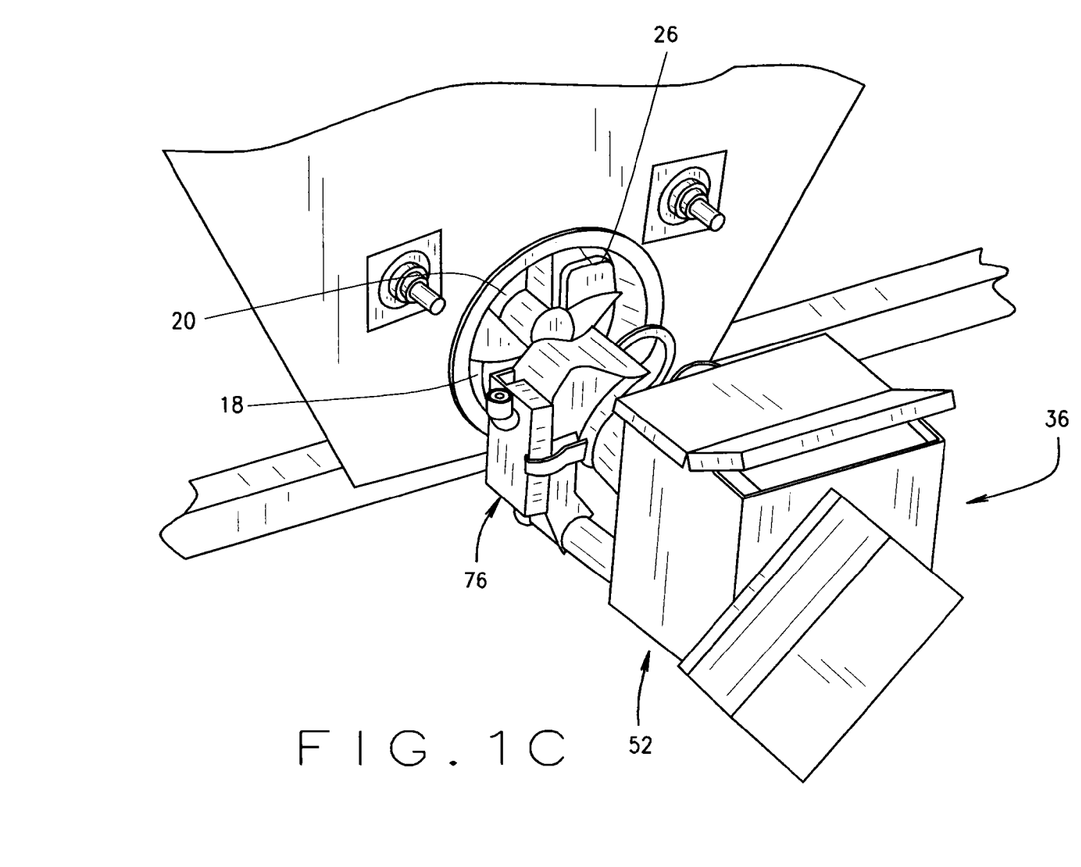
FIG. 1*c* is a front perspective view of the sampler operatively connected to the discharge opening of the grain dryer with the discharge auger tube removed for illustration.

The wet grain is loaded into the garner bin 14 at the top of the dryer 10 by a loading auger or the like. A horizontal auger in the garner bin distributes the grain horizontally such that there is a generally uniform quantity of grain along the length of the garner bin 14 from one end of the dryer to the other. After the grain has traveled downwardly through the grain column and after it has been dried, the dried grain is discharged from the bottom 16 of the grain column. At the bottom of the grain column, metering rolls are provided which are positively driven so as to control the rate at which dried grain is conveyed from the grain column. This, in turn, controls the speed and thus the time that the grain is exposed to the drying air within the grain column. The dried grain is discharged from the bottom of the grain column into a horizontal grain discharge conduit 18. The rate of operation of the metering rolls controls the rate of movement of the grain through the dryer 10 and thus regulates the throughput of the dryer 10. A discharge auger 20 (FIG. 1c) is located in the discharge conduit 18 so as to convey the dried grain from the dryer 10. The dried grain discharged from the dryer is oftentimes deposited in a pickup well (not shown) from which it is conveyed to a holding or conditioning bin by way of another auger conveyor (not shown). It will be appreciated that the grain deposited in such a conditioning bin will be at an elevated temperature such that if ambient air is forced through the still warm grain in the conditioning bin, the grain will oftentimes be dried leading to an additional ½ point of drying compared to its moisture content as it leaves the dryer.

A fan/heater assembly 22 typically includes an axial flow fan which forcefully draws large quantities of air into a relatively large cylindrical housing and forces the air through the housing and into the drying chamber. Although the fan is preferably an axial flow fan, centrifugal fans or other types may also be used. Similarly, although a cylindrical housing is primarily used, other housing shapes such as rectangular or square may also be used. The heater is usually a gas fired burner fueled by liquid propane or natural gas. The burner is located within the cylindrical housing downstream from the fan such that the fuel is burned within the housing and such that the flame and the products of combustion mix with the air flowing through the housing thereby to heat the air to a desired temperature. In certain models of dryers, only a single fan/heater unit is used. In other dryers, two or three fan/heater units, one on top of the other, are employed. In modular stack dryers, two or even three grain dryers as shown in FIG. 1 (which need not all be identical) may be stacked vertically one on top of the other with the grain from the uppermost dryer flowing directly into the grain columns of the next lower dryer with the different dryers being programmed to dry the grain in stages.

A controller 24 for such a dryer 10 must control operation of the inlet auger supplying wet grain to the dryer and the discharge auger 20 carrying away dried grain. The controller 24 must also control the operation of the fan/heater units, the upper and lower grain augers, and the metering rolls. The controller must monitor a number of temperature sensors located in various locations within the dryer so as to enable automatic operation of the dryer to dry the grain to a desired moisture level without overheating the grain (which could cause damage to the grain), and must shut down operation of the dryer in the event certain parameters being monitored by the controller are outside limits established for these parameters corresponding to undesirable operating conditions for the dryer.

A sampler, generally shown as 36 is operatively connected to a discharge opening 26 (FIG. 1c) of the discharge conduit 18. The sampler 36 includes a sampler inlet member 32. The sampler inlet member 32 directs a portion of the grain mass from the discharge opening into a measuring area of the sampler 36 where the moisture content of a representative sample or portion of the grain mass is sensed.

Figure 11:
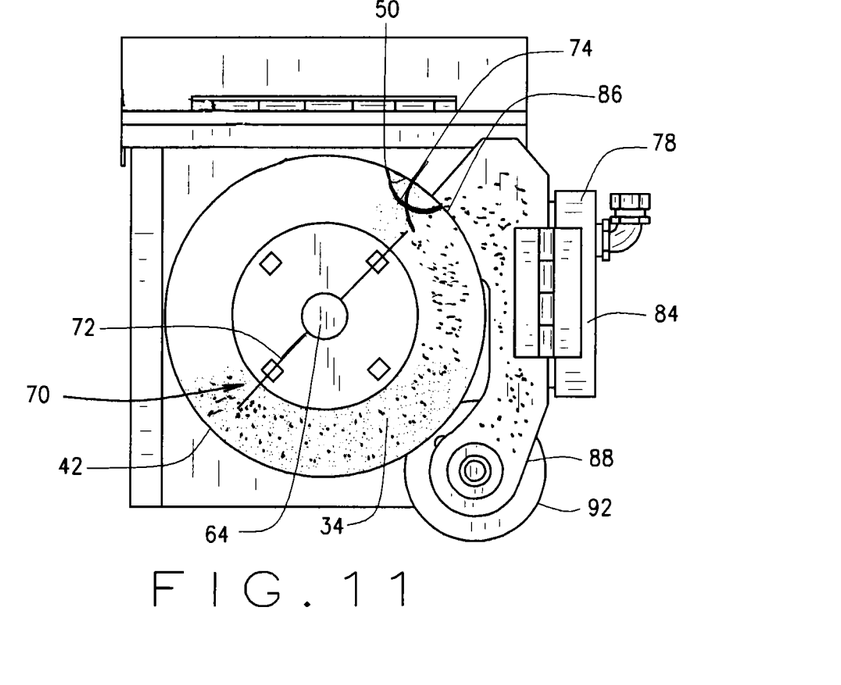
FIG. 11 is front elevational view of the sampler as shown in FIG. 10, but with further portions of the housing removed so as to better illustrate the shape and function of the various components of the sampler, and more particularly to illustrate a fin connected to the primary auger for depositing a portion of the grain mass within the channel into the sensor assembly.
Figure 18:
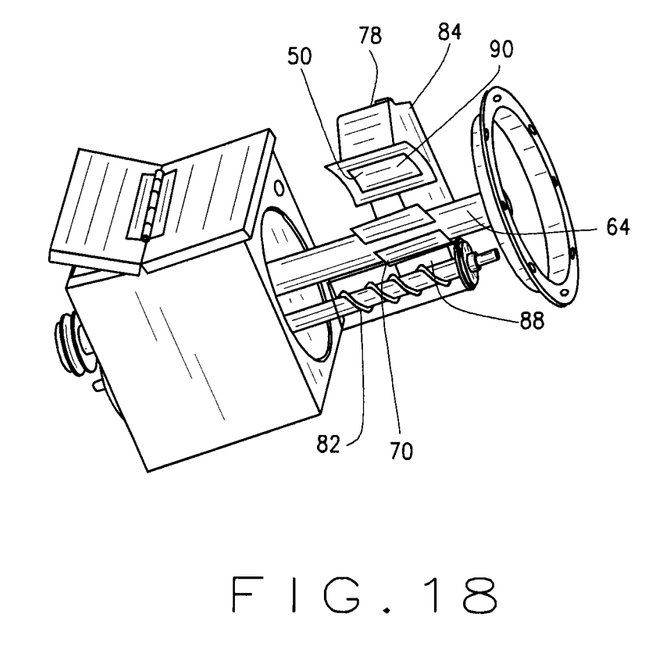
FIG. 18 is a side perspective view of the sampler with portions removed so as to better illustrate the shape and function of the various components of the sampler.

Turning to FIGS. 1d-18, the sampler 36 improves sampling and moisture measurements by reducing the introduction of fines, providing a more representative grain sample, and improving the ability to make consistent moisture measurements. The sampler inlet member 32 is positioned generally horizontally with respect to the discharge conduit 18 of the dryer 10. The sampler inlet member 32 comprises an inlet 38, an outlet 40 and a body 42 disposed between the inlet 38 and the outlet 40. The body 42 has an outer wall 44 and inner wall 46. The inner wall 46 defines a channel 48 which extends through the body 42. The channel 48 includes a sampling opening 50 (FIGS. 11, 12 and 18) extending there through and opening out of the body 42.

Figure 1D:
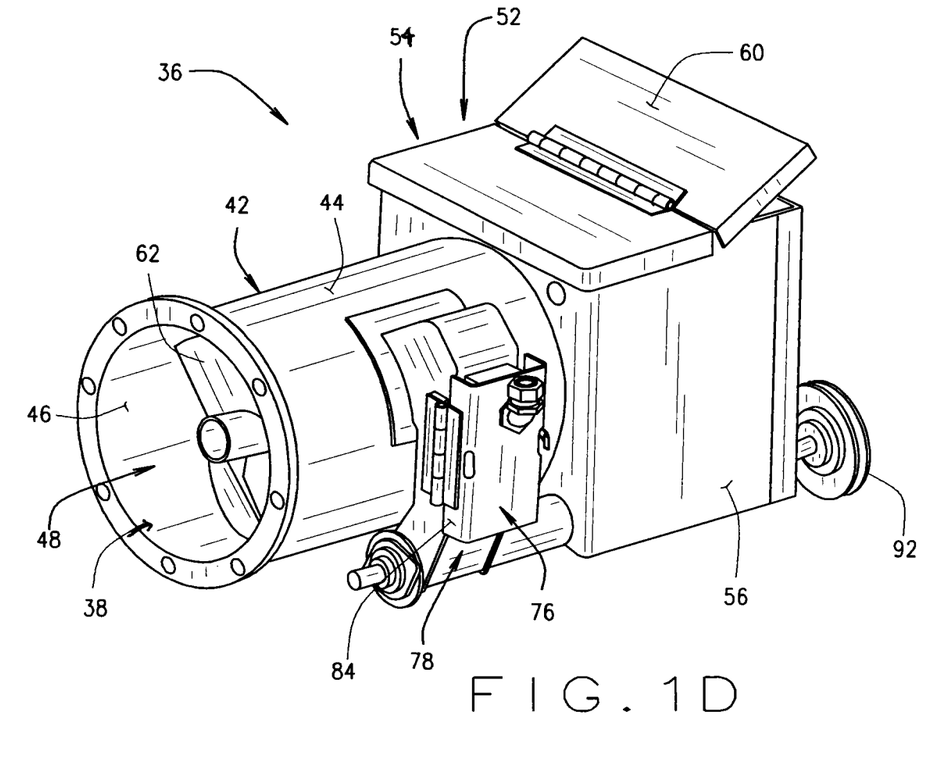
FIG. 1*d* is a side perspective view of the sampler.
Figure 2:
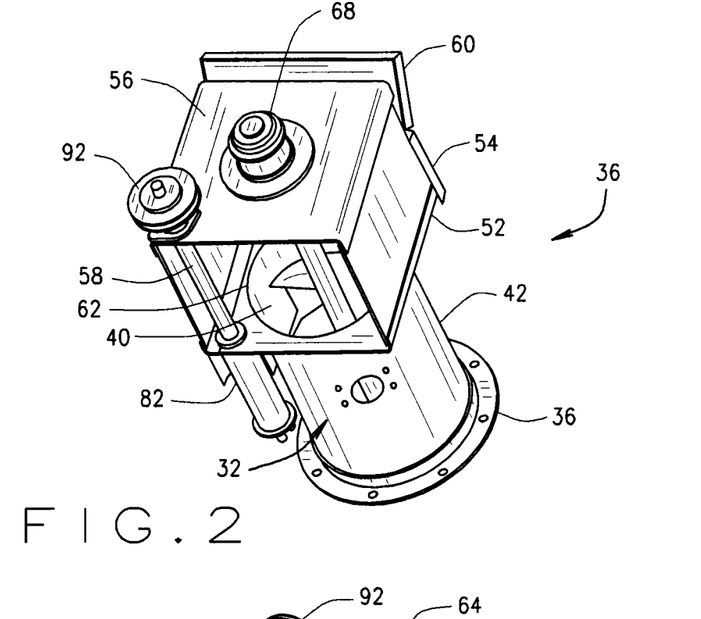
FIG. 2 is a bottom perspective view of the sampler with certain portions of the housing removed for illustration purposes showing a channel, a housing, a primary auger, and a secondary auger.

As illustrated in the figures, a discharge box or housing 52 is operatively connected to the outlet 40 of the body 42. The housing 52 includes a top 54, side walls 56 and an open bottom 58. The open bottom 58 forms a discharge 59 that is in communication with the outlet 40 of the inlet member 32. The top 54 includes a portion 60 defining a rotatable or pivotable access door. As shown in FIGS. 1d and 2, the access door 60 is hinged to a fixed portion of the top 54. As noted in U.S. Pat. No. 5,651,193, the controller can be responsive to the opening of the pivotable door or lid 60 to shut down the dryer when the lid is opened, for example, due to overfilling of the discharge box.

Figure 3:
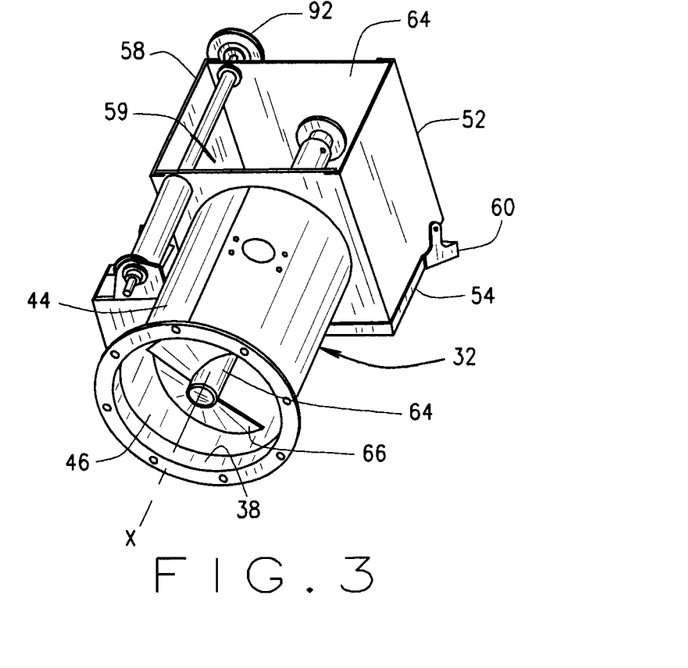
FIG. 3 is another bottom perspective view of the sampler rotated so as to better illustrate a discharge of the housing (with the auger not shown for clarity)
Figure 4:
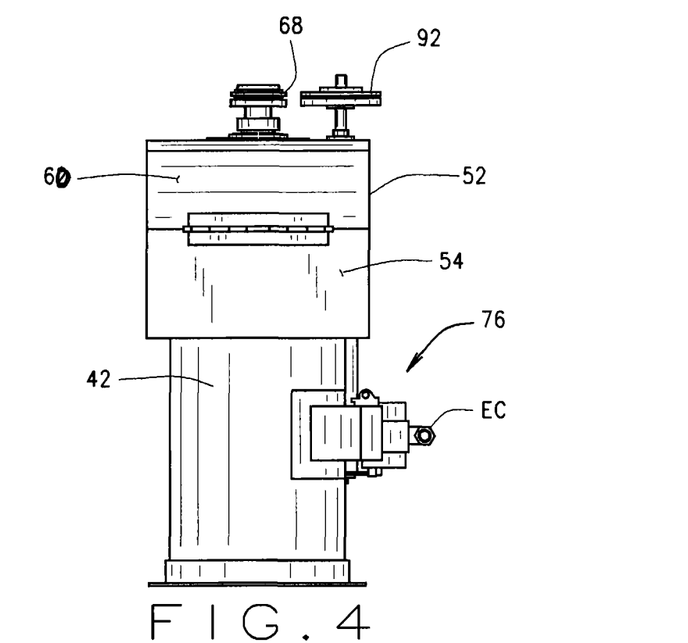
FIG. 4 is top plan view of the sampler illustrating a sensor assembly.
Figure 5:
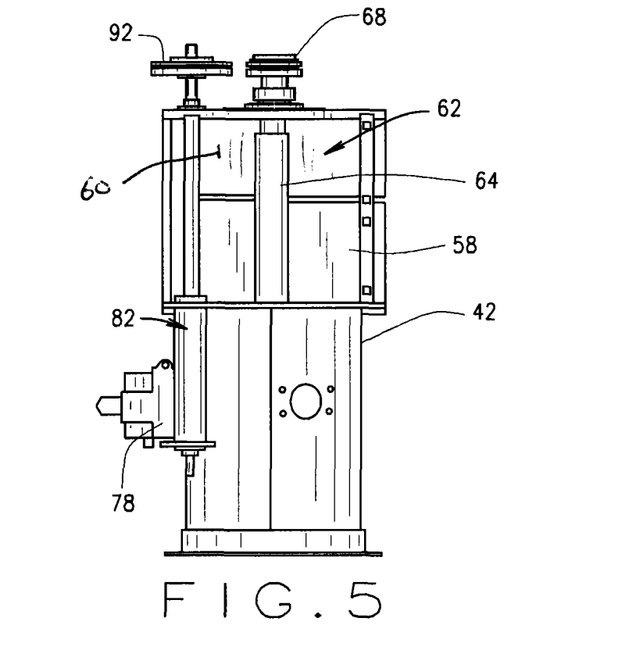
FIG. 5 is a bottom plan view of the sampler illustrating the discharge housing, the sensor assembly, the primary auger and the secondary auger.
Figure 6:
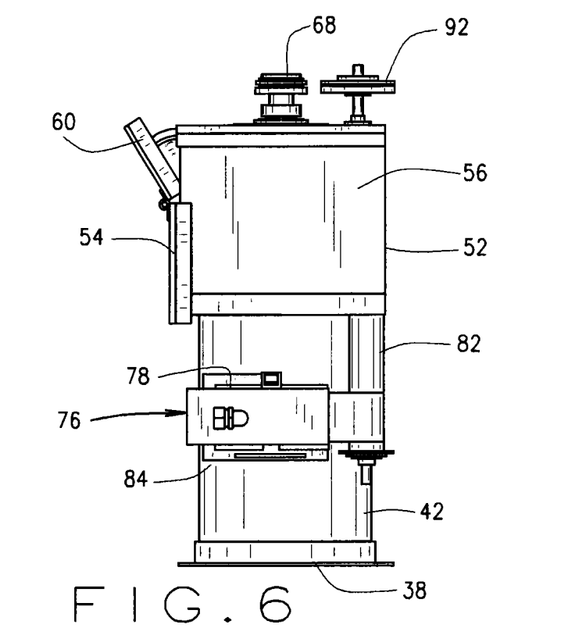
FIG. 6 is a right side elevational view of the sampler.
Figure 7:
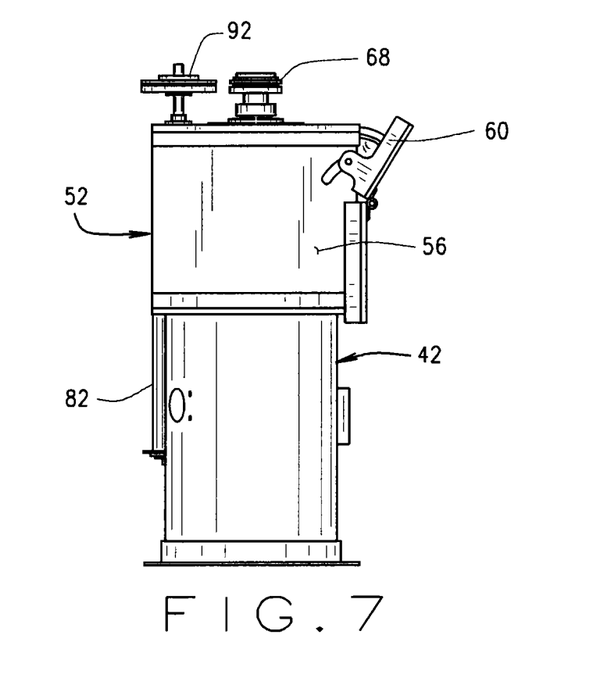
FIG. 7 is a left side elevational view of the sampler.
Figure 8:
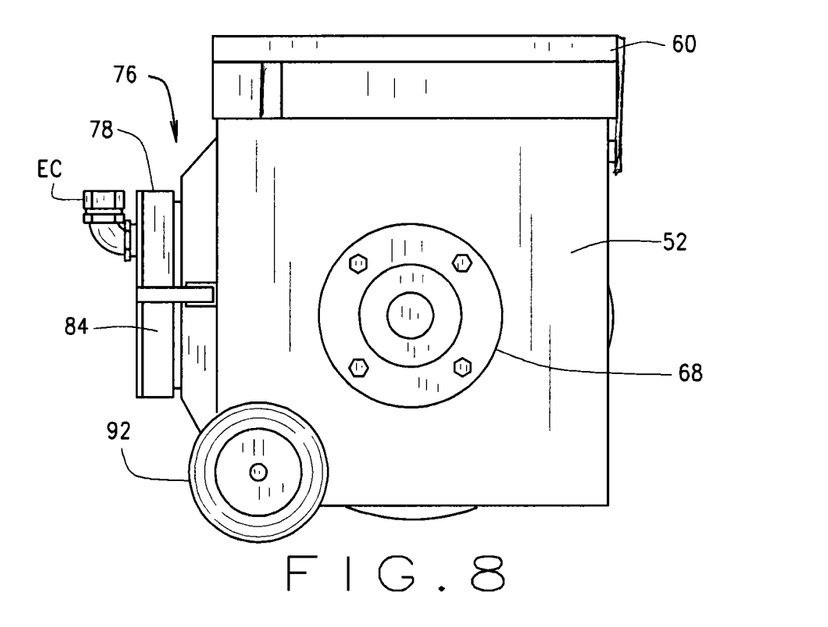
FIG. 8 is a rear elevational view of the sampler.
Figure 9:
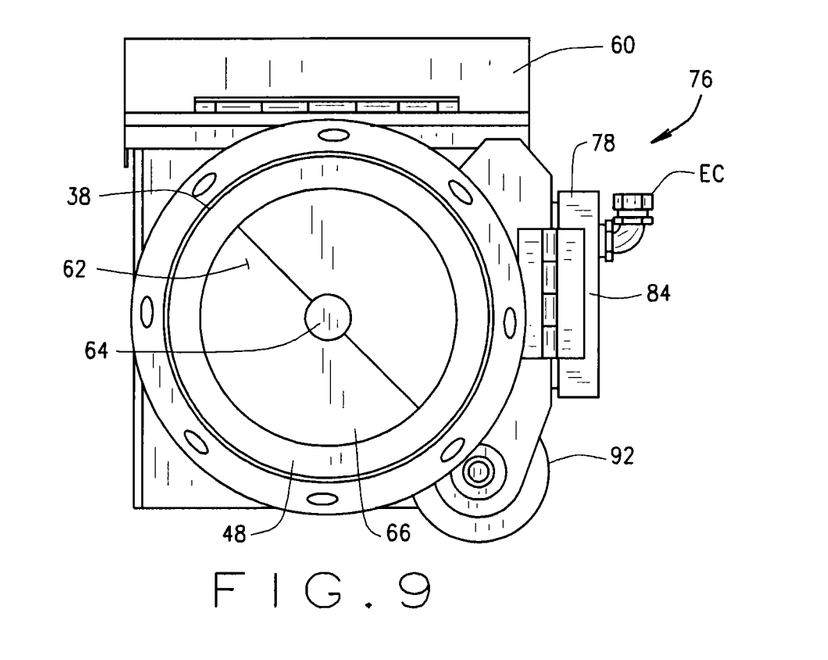
FIG. 9 is a front elevational view of the sampler.
Figure 10:
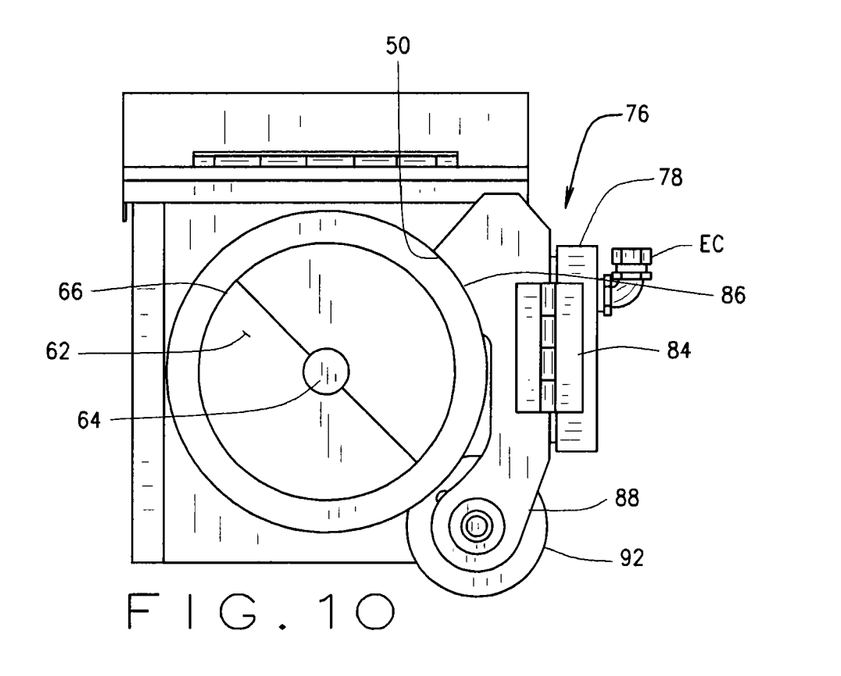
FIG. 10 is front elevational view of the sampler as shown in FIG. 9, but with portions removed so as to better illustrate the shape and function of the various components of the sampler.
Figure 12:
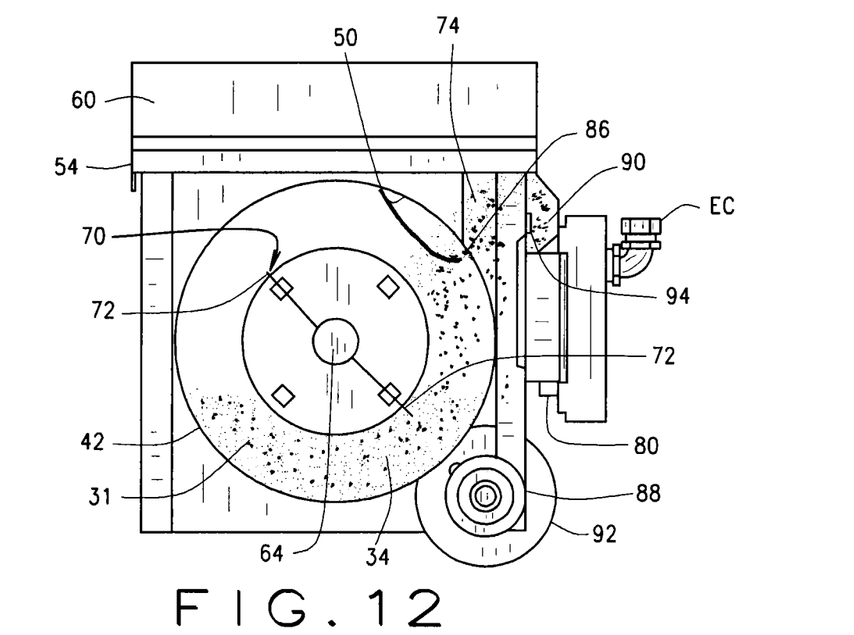
FIG. 12 is front elevational view of the sampler as shown in FIG. 11 with portions removed so as to better illustrate the shape and function of the various components of the sampler, and to more particularly illustrate a portion of the grain mass within the auger tube being lifted and propelled by the fin toward the sampling opening and into the sensor assembly.
Figure 13:
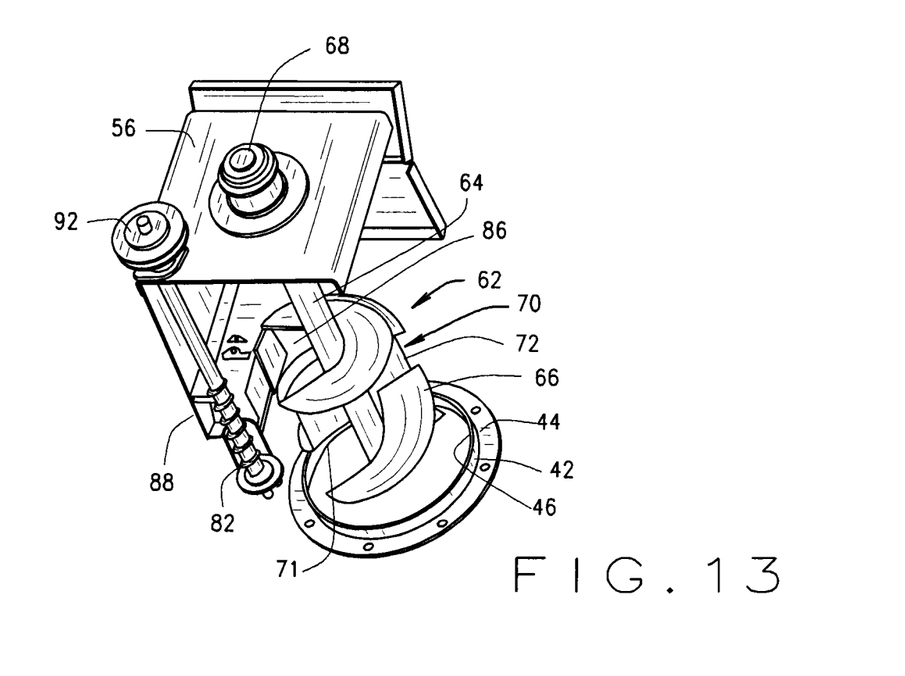
FIG. 13 is bottom perspective view of the sampler with portions removed so as to better illustrate the shape and function of the various components of the sampler.
Figure 14:
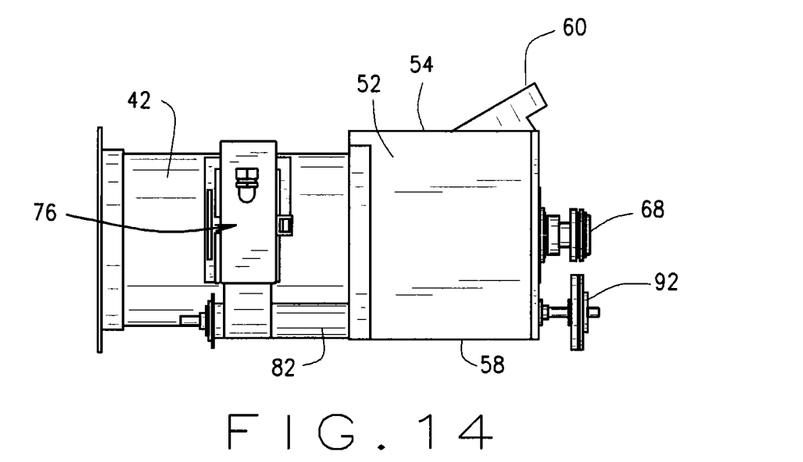
FIG. 14 is a side elevational view of the sampler.
Figure 15:
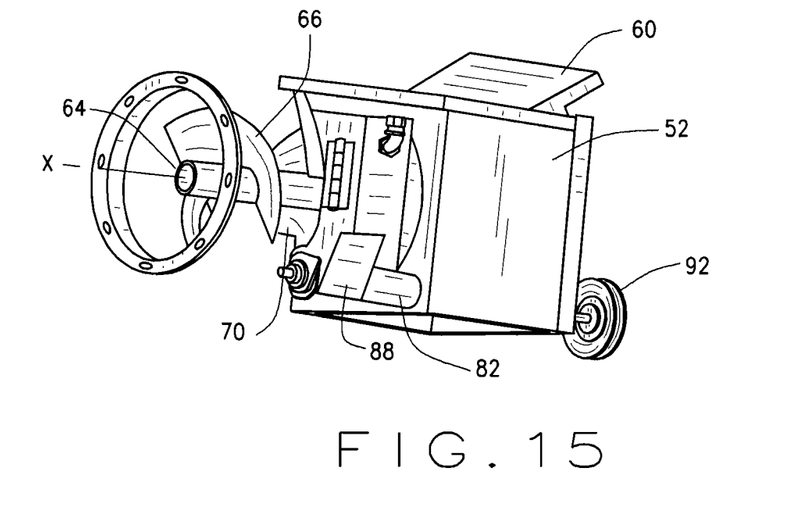
FIG. 15 is a front perspective view of the sampler with portions removed so as to better illustrate the shape and function of the various components of the sampler.
Figure 16:
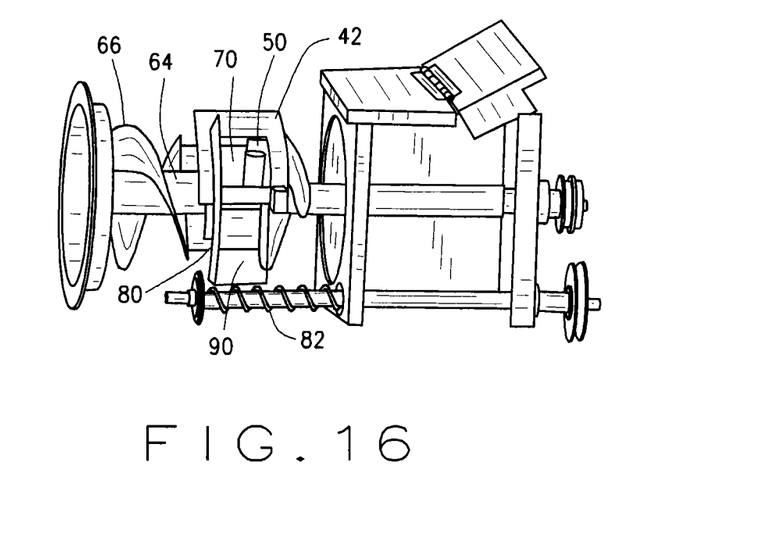
FIG. 16 is a side elevational view of the sampler with portions removed so as to better illustrate the shape and function of the various components of the sampler.
Figure 17:
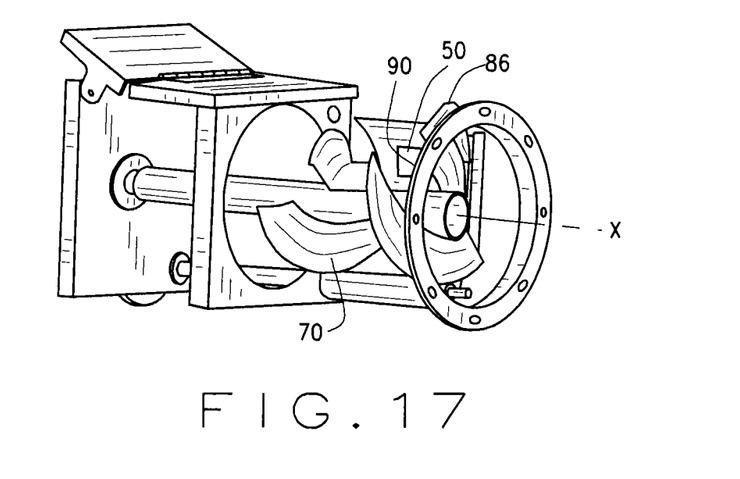
FIG. 17 is a front perspective view of the sampler with portions removed so as to better illustrate the shape and function of the various components of the sampler.

The sampler 36 further comprises a primary auger 62 that is co-axially suspended within the channel 48 of the sampler inlet member 32. The primary auger 62 may be an extension of the discharge/unload auger 20 of the dryer 10. Alternatively, the primary auger 62 may be independent from the discharge auger 20. The primary auger 62 includes a shaft 64 and flighting 66 extending radially outwardly from the shaft 64 (FIG. 13). A motor (not shown) drives the shaft 64 so that the flights 66 move the grain mass 34 (FIGS. 11 and 12) through the channel 48 and toward the discharge bottom 58. The shaft 64 rotates around an auger axis "X", as shown in FIG. 3. As illustrated, one end of the shaft 64 includes a pulley 68 connected thereto. A fin 70 extends radially outward from the shaft 64 between a pair of adjacent auger flights 66. Illustratively, the fin 70 comprises a pair of generally co-planar plates 72 positioned on opposite surfaces of the shaft 64. Thus the fin 70 can comprise a singular plate or a plurality of (i.e., two or more) plates 72 positioned around the shaft 64. The fin 70 has a length, as measured from the shaft 64, which is less than or equal to the radial length of the flighting 66. The fin 70, however, can have a length longer than the flighting 66 but less that the diameter of the inner wall 46 of the body 42. As illustrated, the fin 70 is connected to the shaft 64. Alternatively, the fin 70 can be connected to the pair of auger flights 66. Still further, the fin 70 can be connected to both the shaft 64 and the auger flights 66. The fin 70 can have a variety of shapes such as but not limited to straight or curved portions. Additionally, the fin 70 may include a meshed or slotted portion having a variety of mesh sizes or spacings.

The primary auger 62 moves the grain mass 34 within the channel 48. As seen in FIG. 12, the grain mass 34 does not fill the channel 48, and in fact, the top of the grain mass can be below the shaft 64 of the auger 62. As the auger 62 rotates, the fin 70 is rotated by the shaft 64 into the grain mass 34 to contact the grain mass 34, and then rotates out of the grain mass 34. As the fin 70 rotates out of the grain mass 34, the fin 70 lifts a portion 74 of grain from the grain mass 34, and propels the grain portion 74 of the grain mass 34 toward the sampling opening 50 of the body 42 as will be discussed. As can be appreciated, the fin 70 is shaped and configured to lift the grain portion 74 from the grain mass 34 to deliver or propel the grain portion 74 to the sampling opening 50. After the fin 70 propels the grain portion 74 toward the sampling opening 50, the fin 70 continues to rotate with the auger 62 to contact and to lift another grain portion 74 from the grain mass 34 flowing in the sampler inlet member 32.

The sampler 36 further comprises a sensor assembly 76 that is operatively connected to the body 42. The sensor assembly 76 includes a sensor housing 78, a moisture sensor 80 (FIG. 12) and a secondary auger 82 (FIG. 13). The sensor housing 78 includes side walls 84 (FIG. 10) defining a housing inlet 86, a housing outlet 88 and a chamber 90 (FIG. 12) disposed between the housing inlet 86 and the housing outlet 88. The sensor housing 78 is mounted on the inlet member body 42, such that the sensor housing inlet 86 is in communication with the sampling opening 50 of the inlet member body 42. The sensor housing outlet 88 is in operative communication with the secondary auger 82.

As illustrated in FIG. 13, a pulley 92 is positioned at an end of the secondary auger 82. A belt 93 (FIG. 1B) connects the pulley 68 at the end of the primary auger shaft 64 to the pulley 92 of the secondary auger 82. In this pulley-belt configuration, the shaft 64 of the primary auger 62 directly drives the secondary auger 82. Hence, the motor that drives the primary auger also drives the secondary auger.

The moisture sensor 80 is positioned within the sensor housing chamber 90 wherein an electrical connector EC connects the sensor 80 to a power source and control panel (not shown). The moisture sensor 80 is configured to sense the moisture content of the portion 74 of grain contained within the sensor housing chamber 90 and output a signal indicative of the moisture content of the portion 74 of grain. As is known, this signal is received by the control panel and converted to a percentage moisture content of the grain portion.

In operation, the sampler inlet member 32 receives the grain mass 34 from the dryer discharge 24. The primary auger 62 rotates to move the grain mass 34 within the channel 48 of the sampler inlet member 32 and toward the outlet discharge 40 of the inlet member 32. With the fin 70 rotating with the auger 62, the fin 70 contacts the grain mass 34 to lift or propel a portion 74 of the grain mass 34 toward and through the sampling opening 50 of the sampler inlet member 32. Foreign material or fine material present in the grain mass 34 is lighter than the grain lifted by the fin 70. Consequently, the foreign material or fine material is not propelled into the sampling opening 50; but instead, falls back into the grain mass 34. The grain mass 34 (less the portion 74) continues through the inlet member channel 48 to exit the sampler 36 through the open bottom discharge 59 of the housing 52, where the grain intermixes with the balance of the grain flow. The sensor housing inlet 86 is configured to accept the propelled grain portion 74, and directs this grain into the sensing housing chamber 90. The moisture sensor 80 measures the moisture content of the grain in the chamber 90 as the grain flows through the chamber 90. The sensor housing outlet 88 then directs the grain portion 74 to the secondary auger 82 which moves this grain to the bottom discharge 58 to intermix with the balance of the grain mass 34. The sampler 36 can collect the grain and measure the moisture content of the chambered grain in at least one of continuous batch, staged automatic or continuous flow drying modes. For example, during operation, the chamber 90 is filled and emptied in a batch mode operation wherein the moisture measurements are taken on batches of the chambered grain.

As illustrated, the sampler 36 does not rely on gravity infeed. Instead, the infeed sampling opening 50 is positioned above the level of the grain mass 34 within the inlet member body 42. The moisture sensor 80 is positioned with the small sensor housing chamber 90 adjacent to the inlet member body 42. In proximity to the sampling opening 50, the primary auger 62 is fitted with the fins 70 along the primary auger axis which extend radially toward wall of the inlet member body 42 and which lift the grain portion 74 up to the sampling opening 50. As the fins 70 rotate with the primary auger 62, they are able to lift or elevate a portion 74 or sampling of the moving grain mass 34 toward the sampling opening and deposit the grain portion 74 in the sampling opening 50. In this way, only a portion 74 of the elevated mass 34 will enter the sampling opening 50 while many small fines and particulates will not be elevated by the auger fins 70 and those that are elevated will not likely reach the moisture sensor 80. Accordingly, the accuracy of the readings and measurements by the moisture sensor 80 is improved since the sampler 36 eliminates or substantially reduces the amount of foreign materials, fines and/or particulates which would otherwise be included in the sample that is measured by moisture sensor 80. This reduction of foreign materials, fines and/or particulates provides a more representative grain sample to be monitored.

Once the chamber 90 is full, material that is elevated to the sampling opening 50 will simply fall back into the material flow (i.e., be rejoined with the grain mass 34). The grain in the chamber 90 will behave much as if it was static and its bulk density will not impact the measurement by the moisture sensor 80. The sensor housing outlet 88 of the sensor housing chamber 90 communicates with the secondary auger 82 which removes the grain from the chamber 90 and carries it back to the discharge outlet 40 of the inlet member body 42. This grain then intermixes with the grain mass 34. The use of the horizontal secondary auger 82 permits a more complete, reliable, and measured removal of the grain and particulates in the sampler 36. This ensures that the moisture sensor 78 is presented with a consistent flow of grain, representative of the low or high flow rates of the grain moving by the primary auger 62. In the sampler 36, the speed of the secondary sampler auger 82 is in direct proportion to the speed of the primary auger 62 through the belt and pulley connection, and the sampler 36 is intended to operate in a continuous measurement mode.

In an alternative embodiment, the sampler 36 can be operated in a continuous batch mode with the addition of a fill sensor 94 (schematically shown in FIG. 12) in the chamber 90. In this batch mode operation, a drive mechanism (not shown) engages and disengages the secondary auger 82. The fill sensor 94, such as a capacitive proximity type sensor, is operatively positioned proximate the top of the sampler chamber 90 to detect when the chamber 90 is filled to that level. So long as the fill sensor 94 detects that the chamber 90 is full, the secondary sampler 36 auger would be engaged. Once the fill sensor 94 indicates a determined low level in the chamber 90, the secondary auger 82 would be disengaged, allowing the chamber 90 to be refilled to a sufficient level (i.e., the fill level) as measured by fill sensor. When the chamber 90 is filled, the moisture sensor 80 will sense the moisture content of the grain within the chamber 90. This type of operation would help to ensure that the sampler 36 would never run empty. The engagement and disengagement of the secondary auger 82 could be achieved by a secondary drive system or motor, or could be achieved by the engagement of a clutch to transfer power from the drive of the primary auger 62. Any drive mechanism to engage and disengage the secondary auger 82 is intended to be within the scope of the disclosure.

While the above described sampler has been described as for use in, for example, a grain system, it will be understood by those skilled in the art that the sampling principles described could be applied is a wide variety of applications where it is desired to process a quantity of any dry, solid, fluent or flowable material.

It can be seen that the detailed description of the preferred forms and embodiments of the embodiment fulfill the objects and advantages set forth above. Inasmuch as numerous modifications may be made to the disclosed embodiments without departing from the spirit and scope of the invention, the scope of the invention is to be determined by the scope of the following claims. For example, this sampling strategy could be used to sample a desired level of plastic pellets in an accumulator feeding a plastic molding machine or the like. This example is merely illustrative.

What is claimed is:

1. A sampler for sampling grain from a stream of grain flowing along a path, the sampler comprising:
   a sampler inlet member comprising a body having a body wall, an inlet at a first end of the inlet member, an outlet at a second end of the inlet member, a channel extending between the inlet and outlet, and a sampling opening in the body wall which is in communication with the channel, the sampler inlet member receiving grain from a grain discharge flow path of a grain dryer, the grain received in said inlet member defining a grain level within the inlet member channel; said sampling opening being positioned above the grain level in the sampler inlet member during use of the sampler;
   a primary auger rotatably mounted within the inlet member body, the primary auger having a shaft, an auger flight radially extending outward from the shaft, and a fin operatively mounted to the shaft to extend toward the body wall, the fin comprising a plate configured to lift and propel a portion of the grain up to and through the sampling opening as the auger is rotated within the channel; and
   a sensor assembly on the inlet member body, the sensor assembly comprising an inlet aligned with the sampling opening of the inlet member such that the portion of grain lifted by the fin to the sampling opening will be urged through the sampling opening in the sampler inlet member and into the sensor assembly; the sensor assembly further including a moisture sensor positioned in the sensor assembly to be in contact with grain in the sensor assembly; the moisture sensor generating a signal indicative of the moisture content of the portion of grain.

2. The sampler of claim 1 wherein the fin extends outwardly from the shaft of the primary auger.

3. The sampler of claim 1 wherein the primary auger comprises a pair of auger flights, the fin being positioned between the pair of flights.

4. The sampler of claim 1 wherein the sensor assembly comprises a sensor assembly housing defining a sensor chamber; said sensor assembly inlet being in communication with said sensor chamber; said sensor assembly housing further including an outlet from the sensor chamber.

5. The sampler of claim 4 wherein the connection between the inlet member body and the sensor assembly housing is sealed.

6. A sampler for sampling grain from a stream of grain flowing along a path, the sampler comprising:
   a sampler inlet member having a body with an inlet, an outlet, an inlet member channel extending between the inlet and outlet, and a sampling opening in the body which is in communication with the inlet member channel, the sampler inlet member receiving grain from a grain flow path, the grain received in said inlet member defining a grain level within the inlet member chamber; said sampling opening being positioned above the grain level in the sampler inlet member;
   a primary auger positioned within the inlet member body, the primary auger having a shaft and an auger flighting radially extending outward from the shaft;

a fin radially associated with the primary auger, the fin being configured to lift and propel a portion of the grain up to and through the sampling opening; and a sensor assembly operatively connected to the inlet member body to be in communication with the sampling opening, the sensor assembly being configured to receive the portion of grain propelled through the sampler inlet opening by the fin and including a moisture sensor which generates a signal indicative of the moisture content of the portion of grain; said sensor assembly comprising a sensor assembly housing defining a sensor chamber with an inlet and an outlet to the sensor chamber; the inlet to the sensor chamber being in communication with the sampling opening and a secondary auger in operative communication with the outlet of the sensor assembly.

7. The sampler of claim 6 wherein the primary auger and the secondary auger are in operative communication with the outlet of the inlet member body.

8. The sampler of claim 6 wherein the secondary auger is driven by the primary auger.

9. The sampler of claim 6 wherein the secondary auger is driven by a secondary drive mechanism.

10. The sampler of claim 1 wherein the fin comprises a plurality of fins radially extending outward from the shaft.

11. The sampler of claim 1 wherein the fin has a radial length less than the radius of the inlet member body.

12. The sampler of claim 11 wherein the fin has a radial length that is less than or equal to the radial length of the auger flight.

13. The sampler of claim 1 wherein the fin is either flat or curved.

14. The sampler of claim 1 wherein the fin includes openings.

15. The sampler of claim 14 wherein said openings in the fin are defined by perforations, slots or slits in the fin.

16. The sampler of claim 4 further comprising a fill level sensor in the sensor chamber.

17. The sampler of claim 16 wherein the fill level sensor is in communication with a moisture measurement control system.

18. A method of sampling moisture content of grain from a stream of grain flowing in a path within a sampler inlet member, the method comprising:

moving the stream of grain along the path;

lifting a portion of the grain from the stream of grain to deliver the portion of grain to a sampling opening that is positioned within the sampler inlet member and above the level of the stream of grain in the sampler inlet member;

directing the propelled grain through sampling opening into a sampling chamber; and determining the moisture content of the grain in the sampling chamber using a moisture sensor wherein the moisture sensor generates a signal indicative of the moisture content of the portion of grain.

19. The method of claim 18 further comprising directing the grain in the sampling chamber back into the stream of grain flowing through the sampler inlet member.

20. The method of claim 18 wherein the step of lifting the portion of grain from the stream of grain comprises rotating a fin within the sampler inlet member to contact the stream of grain wherein the fin is configured to lift the portion of grain toward the sampling opening.

21. The method of claim 18 wherein the sampling chamber is filled and emptied in a batch mode operation.

22. The method of claim 21 wherein moisture measurements are taken on batches during the batch mode operation.

23. The method of claim 18 comprising a step of determining when the sampling chamber is filled; the step of determining the moisture content of the grain within the sampling chamber being taken only when it is determined the sampling chamber is filled.

24. The method of claim 23 comprising a step of emptying the sampling chamber after the step of determining the moisture content of the grain has been conducted.

* * * * *